United States Patent [19]

Dal Pont

[11] 4,203,218
[45] May 20, 1980

[54] ENDOSSEAL IMPLANT FOR DENTAL PROSTHESIS

[76] Inventor: Giorgio Dal Pont, Piazza Mazzini 19, 32100 Belluno, Italy

[21] Appl. No.: 914,181

[22] Filed: Jun. 9, 1978

[30] Foreign Application Priority Data

Jun. 10, 1977 [IT] Italy ............................... 84132 A/77

[51] Int. Cl.² ............................................. A61C 8/80
[52] U.S. Cl. ................................................. 433/176
[58] Field of Search ........................................ 32/10 A

[56] References Cited

U.S. PATENT DOCUMENTS

| 693,884 | 2/1902 | Nagy | 32/10 A |
| 3,465,441 | 9/1969 | Linkow | 32/10 A |

FOREIGN PATENT DOCUMENTS

978502  4/1951  France ................................. 32/10 A

*Primary Examiner*—Robert Peshock
*Attorney, Agent, or Firm*—D. Paul Weaver

[57] ABSTRACT

An endosseal implant for the support of an artificial tooth consists of a U-shaped surgical metal wire having a flattened and sharpened bight portion adapted to be hammered into the spongy bone structure forming the alveolar crest. The wire arms of the implant protruding into the oral cavity are shortened, if necessary, and form into occlusion with the opposing teeth and an artificial tooth or teeth are attached to the arms by conventional techniques.

5 Claims, 6 Drawing Figures

ENDOSSEAL IMPLANT FOR DENTAL PROSTHESIS

BACKGROUND OF THE INVENTION

Various forms of implants for dental prosthesis are known in the prior art including screws, needles and blades upon which artificial teeth may be supported in the oral cavity following insertion of the implant into the bony structure which normally supports the natural teeth. The prior art devices all possess certain disadvantages such as excessive cost, complexity of construction and difficulty of implantation into bone. These difficulties require the use of different types and shapes of implants for different regions of the jaws to accommodate variations in bone thickness. Also appreciable surgical trauma may result from the implantation procedures of the prior art.

Therefore, the objective of this invention is to improve on the known prior art by providing a more economical, convenient and more versatile endosseal implant for dental prosthesis, the use of which lessens surgical trauma. Essentially, the same implant structure can be used at all points along the dental arch and variations in bone thickness do not detract from the efficiency of the implant.

Various features of the invention will become apparent during the course of the following description.

SUMMARY OF THE INVENTION

A length of surgical metal wire is formed into a U shape with the bight of the U flattened and provided with a sharp external transverse edge, such edge being substantially perpendicular to the sides or arms of the U-shaped formation. Following proper surgical preparation, the sharpened bight portion is hammered into the alveolar crest to a sufficient depth to provide a firm and stable rest. The arms of the implant which project into the oral cavity can then be shortened, if necessary, and bent into proper occlusion with opposing teeth and the arms then serve to support the artificial tooth applied thereto by conventional techniques.

DETAILED DESCRIPTION

Figures 1, 2, 3:
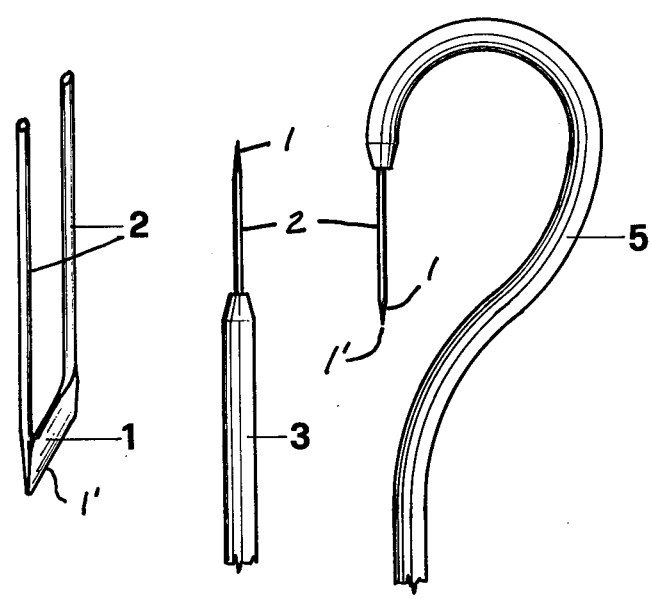
FIG. 1 is a perspective view of an endosseal implant embodying the invention.
FIG. 2 is a side elevation of an inserting instrument for an upper jaw implant according to the invention.
FIG. 3 is a side elevation of an inserting instrument for a lower jaw implant.

Referring to the drawings in detail, wherein like numerals designate like parts, a basic form of the endosseal implant shown in FIG. 1 is constructed of surgical metal wire, preferably about 1 mm. in diameter, formed into the general shape of a U. The bight portion 1 of the U-shaped wire implant is flattened and provided with a sharp straight external transverse edge 1' disposed substantially at right angles to the two approximately parallel arms or sides 2 of the U-shaped implant. For most generalized use, the U-shaped implant has a width of about 4 mm. along the sharpened edge 1' and a length of about 35 mm. along the arms 2. These dimensions can be varied slightly. The flattened sharpened bight portion 1 is the implant is chisel-like to facilitate hammering into the bony structure of the alveolar crest.

To facilitate the implantation procedure, a straight upper jaw inserting instrument 3, FIG. 2, and a curved lower jaw inserting instrument 5 are provided. Both instruments have passages to receive and hold the arms 2 of the implant therein with the chisel-like bight portion 1 projecting therefrom, as illustrated.

Figures 4, 5, 6:
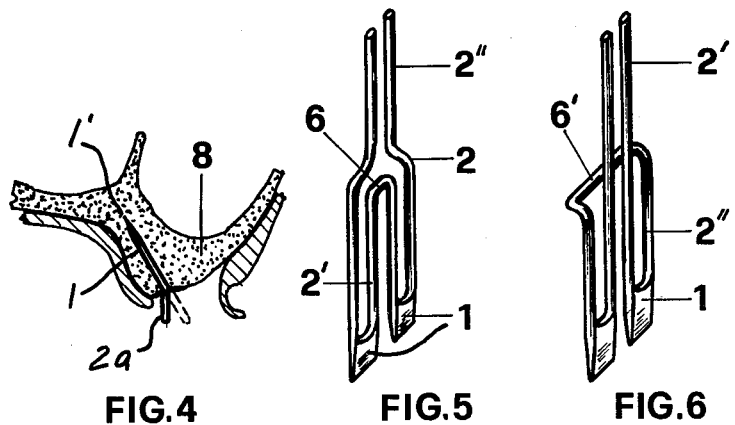
FIG. 4 is a partly diagrammatic cross section taken through the upper jaw with the implant installed in the spongy bone structure.
FIG. 5 is a perspective view of an implant according to a modification of the invention.
FIG. 6 is a similar view of an implant according to a further modification.

The insertion of the implant shown in FIGS. 1 to 3 into the supporting bone structure 8 of the upper jaw, FIG. 4, is carried out as follows:

After having bores through the cortical plate of the exposed alveolar crest, a fine fissure whose length corresponds to that of the bight portion 1 of the implant, namely about 4 mm., is formed. The sharpened edge 1' of the implant is inserted into this fissure and sunk into the bone 8 by hammering on the inserting instrument 3 or 5, until a sufficient depth is reached in the bone to form a firm and stable rest for the implant. After such implantation, the arms 2 which protrude into the oral cavity are shortened, if necessary, and bent into proper occlusion with opposing teeth, as indicated at 2a, FIG. 4. Following such formation, the artificial teeth, not shown, are applied to the projecting elements 2a by known techniques.

The implant for dental prosthesis in accordance with the above description offers the following advantages over the prior art:

(1) Simpler realization.
(2) Easier insertion in the bony structure.
(3) Less injury to the bone tissue.
(4) Larger possibility of use in all regions of the upper and lower jaws regardless of variations in bone thickness around the dental arch.
(5) Greatly reduced danger of deep germ penetration because of the reduced connection between the implant and the oral cavity as a consequence of the thinness of the sections protruding into the oral cavity.
(6) Smallest possible amount of foreign material is introduced into the body of the host.

As shown in FIGS. 5 and 6, the endosseal implant can be realized in a side-by-side pair of coupled units in which the internal vertical segments 2', FIG. 5, and the external segments 2", FIG. 6, are connected together to form transverse bars 6 and 6' which can rest on the alveolar crest following installation of the implant. The external segments 2", FIG. 5, and the internal segments 2', FIG. 6, are employed to support the artificial teeth.

In essence, therefore, the invention consists of a unitary section of surgical metal wire formed into a U and having a flattened sharp chisel-like bight at right angles to the two arms of the U, the implant being formed either as a single unit or as two side-by-side coupled units having a common transverse bar element for resting on the alveolar crest.

It is to be understood that the forms of the invention herewith shown and described are to be taken as preferred examples of the same, and that various changes in the shape, size and arrangement of parts may be resorted to, without departing from the spirit of the invention or scope of the subjoined claims.

I claim:

1. An endosseal implant for dental prosthesis which requires no incising and pre-drilling of the gum tissue and jaw bone comprising a unitary surgical round metal wire section having a diameter of about one millimeter including a pair of bendable and trimable substantially parallel and substantially equal length segments, and a flattened chisel-like transverse anchor portion integrally joined to corresponding ends of said parallel segments and having a straight sharpened edge along that side of the anchor portion away from said segments, the anchor portion being formed from the same unitary wire section used to form the parallel segments and being produced solely by flattening and sharpening such wire section, said anchor portion adapted to be driven by impact into the bone structure forming the alveolar crest.

2. An endosseal implant for dental prosthesis as defined in claim 1, wherein the length of said anchor portion and sharpened edge thereof is about four millimeters.

3. An endosseal implant for dental prosthesis as defined in claim 2, and wherein the length of said implant measured along said segments is about thirty-five millimeters.

4. An endosseal implant for dental prosthesis as defined in claim 1, and said implant including two side-by-side coupled units each having a flattened sharpened edge anchor portion carried by pairs of spaced parallel wire segments with the inner segments of the pairs joined by a common transverse wire element adapted to rest on the alveolar crest, and said first-named parallel equal length segments extending from and being integral with the outer segments of said pairs.

5. An endosseal implant for dental prosthesis as defined in claim 1, and said implant including two side-by-side coupled units each having a flattened sharpened edge anchor portion carried by pairs of spaced parallel wire segments with the outer segments of the pairs integrally joined by a common transverse wire element adapted to rest on the alveolar crest, and the interior segments of said pairs extending away from said anchor portions and forming toothed supports.

* * * * *